(12) United States Patent
Calhoun et al.

(10) Patent No.: US 6,280,198 B1
(45) Date of Patent: Aug. 28, 2001

(54) REMOTE COMPUTER IMPLEMENTED METHODS FOR COGNITIVE TESTING

(75) Inventors: Barbara Calhoun, Berkeley; Bret E. Peterson, Lafayette; Michael M. Merzenich, San Francisco, all of CA (US)

(73) Assignee: Scientific Learning Corporation, Oakland, CA (US)

( * ) Notice: Subject to any disclaimer, the term of this patent is extended or adjusted under 35 U.S.C. 154(b) by 0 days.

(21) Appl. No.: 09/241,362

(22) Filed: Jan. 29, 1999

(51) Int. Cl.[7] .................................................. G09B 19/00
(52) U.S. Cl. ......................... 434/236; 434/350; 434/322; 434/323; 434/362
(58) Field of Search ..................... 434/236, 350, 434/322, 323, 258, 362, 335

(56) References Cited

U.S. PATENT DOCUMENTS

| 5,711,671 | * | 1/1998 | Geeslin et al. ............ 434/236 X |
| 5,725,472 |   | 3/1998 | Weathers . |
| 5,911,581 |   | 6/1999 | Reynolds et al. . |
| 5,940,801 |   | 8/1999 | Brown . |
| 5,957,699 | * | 9/1999 | Peterson et al. .......... 434/350 X |
| 5,961,332 | * | 10/1999 | Joao ....................... 434/236 X |
| 6,030,226 |   | 2/2000 | Hersh . |
| 6,052,512 | * | 4/2000 | Peterson et al. .......... 709/220 X |
| 6,053,739 |   | 4/2000 | Stewart et al. . |
| 6,063,028 | * | 5/2000 | Luciano ................... 600/300 X |

FOREIGN PATENT DOCUMENTS

| WO 87/07969 | 12/1987 | (EP) | .............. G06F/15/42 |
| WO 92/13487 | 8/1992 | (EP) | .............. A61B/5/16 |
| WO 95/29447 | 11/1995 | (EP) | .............. G06F/15/02 |

* cited by examiner

*Primary Examiner*—Michael O'Neill
*Assistant Examiner*—Chanda Harris
(74) *Attorney, Agent, or Firm*—Beyer Weaver & Thomas

(57) ABSTRACT

The invention relates to a computer implemented method for remotely administering and monitoring cognitive tests on a person using a computer network having a remote computer and a remote administering computer. The computer-implemented method includes administering a set of baseline cognitive tests to the person. The method further includes repeatedly administering a set of cognitive tests, obtaining a performance response of the person to the tests and uploading the testing information via the computer network. The method may also include monitoring the performance of the person. A database may be built from the performance response of multiple persons. The computer-implemented method includes administration using at least two computers where at least one is local and the other is remote.

20 Claims, 5 Drawing Sheets

| Test Subject | Test Subject Demographic Information | Baseline Testing | | | | Testing | | | |
|---|---|---|---|---|---|---|---|---|---|
| | | Day 1 | Day 2 | ... | Day N | Day 1 | Day 2 | ... | Day M |
| #1 | | | | | | | | | |
| #2 | | | | | | | | | |
| #3 | | | | | | | | | |

REMOTE COMPUTER IMPLEMENTED METHODS FOR COGNITIVE TESTING

BACKGROUND OF THE INVENTION

The present invention relates generally to techniques for cognitive testing. More particularly, the present invention relates to remote computer implemented methods for cognitive testing and building a cognitive testing database to aid in assessing changes in a person's cognitive status.

Generally speaking, a cognitive skill may be defined as a decision that takes time to process. There are different components of cognitive skills including, for example, short term and long term memory, planning/prediction, switching, speed, and spatial orientation. Cognitive testing is well established and there exists an abundant number of cognitive tests that measure the different cognitive skills. Conventionally, the testing of cognitive skills consists of a battery of tests. For example, the IQ test is part of cognitive testing. Another example is the game Tetris, which may test the cognitive skills of mental rotation and speed.

For a potential monitoring program, for example, monitoring a person at risk for a disorder that affects cognition, such as depression, or monitoring a person using biochemical based therapy, where hundreds of different alternatives may be selected from, evaluation may be desirable. Subtle changes in a person's cognitive skills may predict an impending change in their disorder or undesirable side effects from their therapy, allowing timely intervention. In addition, it is often desirable to administer a particular therapy program that has the least undesirable side affects or to intervene with a therapy in case of the immanent occurrence of an acute crisis in a previously static situation. As different therapy programs may have different effects on specific cognitive skills, it is desirable to determine which cognitive skills, and to what extent these cognitive skills, are affected by a particular alternative, and then elect a therapy program which may fit the person's needs best, or elect to intervene in a previously static condition.

One possible method for measuring the efficacy of a therapy program is to monitor potential changes in cognitive skills through cognitive testing. For example, for a person taking a new therapy program, cognitive testing may allow monitoring and potentially useful feedback of either program efficacy or the presence of side affects due to the therapy.

In the past, testing of cognitive skills motivated by therapy programs has been limited to low frequency testing such as manual testing, which usually consists of face-to-face testing in a testing site such as a physician's office, for example. The testing frequency is then governed by the convenience or ability of the person to travel to the testing site. In another costly manner, the person may remain in a hospital for high frequency testing of cognitive skills, but the dramatic costs of inpatient health care may make this alternative prohibitively expensive. For these reasons, cognitive testing frequency was usually limited to one test before treatment inception and one test once again several weeks to months afterwards.

Aside from the traditional face-to-face testing, there are current techniques that use computer implemented methods for cognitive testing. The Neurobehavioral Evaluation System (NES2) as described by Baker et al. of Atlanta, Georgia is a computer-implemented method for testing cognitive skills on a low frequency basis. The testing is administered at a testing site and testing frequency is again limited by the person's ability to travel to the testing site. Thus, for assessing the effects of a therapy program for example, one disadvantage to the NES method is that practical considerations of administering the test at a testing site do not allow for monitoring the affects of the therapy program on a frequent basis.

Current cognitive testing methods do not facilitate high frequency cognitive skill assessment in the presence of therapy programs. For the case when monitoring of the cognitive skills is required on a daily basis, testing at a testing site is undesirable since it requires an inconvenient amount of travel for the person. In addition, practical considerations may also limit the frequency of testing when the time to travel to the testing center is longer than the testing duration. A further disadvantage of testing cognitive skills at a testing site, for example, for cases of chronic biochemical based therapy (such as asthma medication) is the potential undesirable side effects (i.e. drowsiness) of the therapy, which may affect the person's ability to travel to the testing site.

In view of the foregoing, there are desired improved techniques for administering and monitoring high frequency cognitive testing in a convenient and cost-effective manner.

SUMMARY OF THE INVENTION

The invention relates, in one embodiment, to a computer-implemented method for remotely administering and monitoring cognitive tests on a person using a computer network having a remote computer and a remote administering computer. The method includes repeatedly administering a set of cognitive tests, obtaining a performance response of the person to the tests and uploading the testing information via the computer network.

In another embodiment of the present invention, the invention relates to a computer implemented method for remotely administering and monitoring cognitive tests on a person using a computer network having a remote computer and a remote administering computer. The computer-implemented method includes administering a set of baseline cognitive tests to the person. The computer-implemented method further includes repeatedly administering a set of cognitive tests, obtaining a performance response of the person to the tests and uploading the testing information via the computer network.

In yet another embodiment of the present invention, the invention relates to a computer implemented method for remotely administering and monitoring cognitive tests on a person using a computer network having a remote computer and a remote administering computer. The computer-implemented method includes administering a set of baseline cognitive tests to the person. The method further includes repeatedly administering a set of cognitive tests during therapy, obtaining a performance response of the person to the tests and uploading the testing information via the computer network. The method also includes monitoring the performance of the person.

Embodiments of the present invention further relate to a computer readable medium including instructions for remotely administering and monitoring cognitive tests on a person using a computer network having a remote computer and a remote administering computer. The instructions may include instructions for repeatedly administering a set of cognitive tests, obtaining a performance response of the person to the tests and uploading the testing information via the computer network.

Embodiments of the present invention also relate to delivering computer readable instructions for remotely administering and monitoring cognitive tests on a person using a computer network having a remote computer and a remote administering computer. Transmission of signals may include instructions for repeatedly administering a set of cognitive tests, obtaining a performance response of the person to the tests and uploading the testing information via the computer network.

These and other advantages of the present invention will become apparent to those skilled in the art upon a reading of the following descriptions of the invention and a study of the several figures of the drawing.

BRIEF DESCRIPTION OF THE DRAWINGS

The present invention is illustrated by way of example, and not by way of limitation, in the figures of the accompanying drawings in which:

FIG. 5 illustrates, in accordance with one aspect of the present invention, the structure of a database for storing the results of the computer implemented cognitive testing method.

DETAILED DESCRIPTION OF THE PREFERRED EMBODIMENTS

Figure 1A:
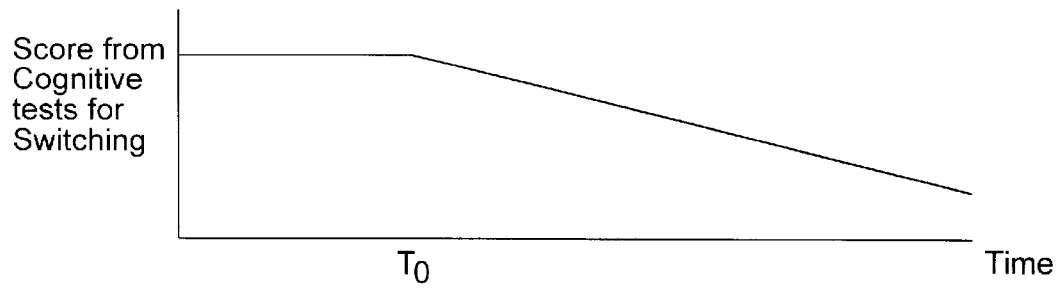
FIGS. 1a–c illustrate, in accordance with one embodiment of the present invention, exemplary responses to cognitive testing of different cognitive skills for a sample biochemical based therapy program.

The present invention will now be described in detail with reference to a few preferred embodiments thereof as illustrated in the accompanying drawings. In the following description, numerous specific details are set forth in order to provide a thorough understanding of the present invention. It will be apparent however, to one skilled in the art, that the present invention may be practiced without some or all of the specific details. In other instances, well known process steps and/or structures have not been described in detail in order not to unnecessarily obscure the present invention.

In accordance with one aspect of the present invention, there are provided techniques for remote computer implemented methods of administering cognitive tests. This type of cognitive testing may be useful, for example, for companies looking to monitor the effects of biochemical based therapy on a person. For a potential therapy program, where hundreds of different alternatives may be selected from, it may be desirable to administer the most effective therapy program with the least undesirable side effects. As certain particular therapy programs may affect separate cognitive skills, the goal then, in one embodiment of the present invention, is to determine which, and to what extent, cognitive skills are affected by a potential therapy program, and then elect a therapy program which fits the person's needs best.

As an example, for an epilepsy therapy program, where a specific region of the brain may be targeted as the focal point of the hyperactivity problem, an anti-convulsant biochemical based therapy program may be administered such that it targets the desired focal point of the brain. On the other hand, it may be possible for this alternative to undesirably affect other regions of the brain that are responsible for certain cognitive skills. Thus, the goal for finding a therapy program for epilepsy in this case then may be to find an alternative which affects the desired focal area of hyperactivity but does not unduly affect reaction time, balance, or any ability to carry out daily activities such as driving or any other cognitive skill that may affect normal lifestyle.

It may be advantageous to measure therapy program efficacy by measuring cognitive skills via cognitive testing at a high frequency. In this manner, cognitive skills may be monitored for a period of time before and after inception of a particular therapy program and may be used to compare personal performance with and without the effect of the therapy. A further advantage of high frequency cognitive testing is higher resolution of cognitive skill data and earlier feedback of effects of the therapy program. This may allow earlier intervention if necessary, which may advantageously prevent long periods of exposure to negative side effects that would be felt in the case of low frequency testing. In addition, high frequency testing may allow for detection of a change in cognitive skills before the person is aware of it. The high frequency testing also allows for noise or random inputs in the testing to be filtered out, which may provide a more accurate measure of the person's cognitive skills. This is advantageous over the prior art methods where discreet cognitive testing results are used to evaluate performance, or are used to compare a human subject's performance to discreet results from a large population.

For conventional manual testing methods, and similarly for testing with the NES2 method, the tests are commonly administered at a testing site wherein practical considerations may limit the possibility or frequency of testing. In one embodiment of the present invention, a networked remote computer is used to administer the cognitive testing. By remote (i.e. local to the human subject) testing on a frequent basis, the practical inconveniences and potential inaccuracies of prior art testing techniques are advantageously avoided.

Not only does the use of a remote computer allow for high frequency testing, it further permits other novel benefits. Due to the convenience of the remote computer implemented cognitive testing techniques, it may be possible to administer the cognitive tests in less time that it would take to travel to a testing center. In addition, the remote cognitive testing on a high frequency basis may also allow for improved clarity of assessment by screening out random variation such as varying test times, fatigue due to travel, or mental factors involved in testing a person in an unfamiliar setting such as a hospital or an office.

The novel concept of high frequency cognitive testing may also introduces new demands addressed by the present invention. For cognitive tests administered at a high frequency, it is desirable for testing to be administered in a manner to engage the person sufficiently. For example, it is desirable for testing to be administered in a manner in which the person's intensity and focus is not diminished over the testing session. Thus, it is desirable for the testing method and tests chosen prior to testing, or selected during baseline testing as described below, to be sensitive to the human subject's personal engagement levels.

As there is no current technique for convenient, cost-effective high frequency testing of cognitive skills, there is no means for collecting results based on high frequency testing. Collection of high frequency cognitive testing results may also permit the potential to build a database that contains testing information for a large number of people. This information may then be useful in future assessment and election of proposed therapy programs.

Although response to a therapy program may vary from person to person, there may be trends in response to a therapy program that are common for a demographic group. It is then desirable, in one embodiment of the present invention, to test the response of a human subject belonging to a specific demographic group to a therapy program. In this manner, the efficacy of the therapy program for a large number of people belonging to that demographic group may be monitored and assessed. In a further embodiment of the present invention, the database may be used to predict potential suitability of therapy programs or aid in selecting a therapy program which fits a person's needs based on their demographic status best.

One advantage of building a database is that general improvements of a large number of human subjects may be used to correlate an expected improvement for a demographic group. This general trend extrapolated from the database information may then be used in future administration to help predict and interpret the response of a therapy program. In other words, if the human subject does not produce an expected result in comparison to the trends stored in the database for a large number of people, the database information may be used to signal a potential discrepancy for the current human subject. For example, for repetitive administration of the same test over time for a human subject, improved performance in a human subject is expected. In this case, the database may be used to detect an abnormal performance.

In one embodiment of the present invention, prior to inception of a therapy program, a set of baseline cognitive tests may be administrated. In this manner, a reference performance of the human subject may be established without the variable affect of the therapy. Baseline testing is preferably performed daily for one week prior to therapy inception. Baseline testing may include testing the human subject's response to a large number of cognitive tests in order to determine from a number of tests which tests elicit a high level of engagement. As an example, ten different cognitive tests may be administered during baseline testing, and three tests may be selected from these ten that may best maintain a high level of engagement in the subject. In one embodiment of the present invention, the baseline cognitive testing is administrated using a remote computer.

After inception of the therapy program, the cognitive testing is continued using the remote computer that is networked with the computer employed to monitor testing progress. In one embodiment of the present invention, the computer implemented cognitive tests may take the form of a set of trials or games that the human subject plays on a remote computer. As an example, the computer implemented cognitive tests may take the form of three games the person plays on a daily basis for four minutes. The cognitive tests may be transmitted to the remote computer and the information presented in this case is the testing data provided a monitoring computer. In another embodiment of the present invention, after inception of the therapy, the person may remain on the same regiment playing the games at the same time every day. The testing performance and data may then be returned from the remote computer to the monitoring computer site and may be used as appropriate (i.e. for further analysis).

It is important to note that cognitive testing is well established. Thus, there are numerous cognitive tests that may be applied using the remote computer implemented testing methods. In order to maintain a high level of engagement, a test may be chosen that previously have been shown to be associated with a high level of engagement. For example, Tetris may be used as a cognitive test for the cognitive skills of spatial orientation and reaction time as tests associated with a high level of engagement.

A cognitive test may test for more than one cognitive skill. As an example, one type of cognitive test used in the proposed remote computer implemented method is a maze-type game. The configuration of the maze-type game allows the rules to be changed such that the test may probe different cognitive skills. For example, a maze may be used that has many starting points at one end of the maze and a single exit at the other end of the maze. If the test rules are designed such that the person is penalized for entering and not successfully exiting, then the game may test the person's ability to plan. A further example is if the rules of the maze game are altered. For example, if input from the human subject is reversed such that right becomes left, and left becomes right, the game may test for a person's ability to adapt to rule changes or the cognitive skill of switching. A third example of a cognitive skill that the maze game may test is speed. In this case, the person's ability to exit the maze is timed.

In one embodiment of the proposed invention, the games used in the remote computer implemented cognitive testing method orthogonally test for different components of cognitive skills. In this manner, isolation of the different cognitive skills may be achieved. As an example, three tests of cognitive skills may be provided, one which may test for short-term memory, the second which may test for switching (the ability to adapt to the rules of a cognitive test or game), and the third may test for spatial orientation. After testing, the testing data and the testing results may be transmitted to a monitoring computer where a database may store all testing results, permitting an administrator to monitor the person's performance over time.

Figure 1B:
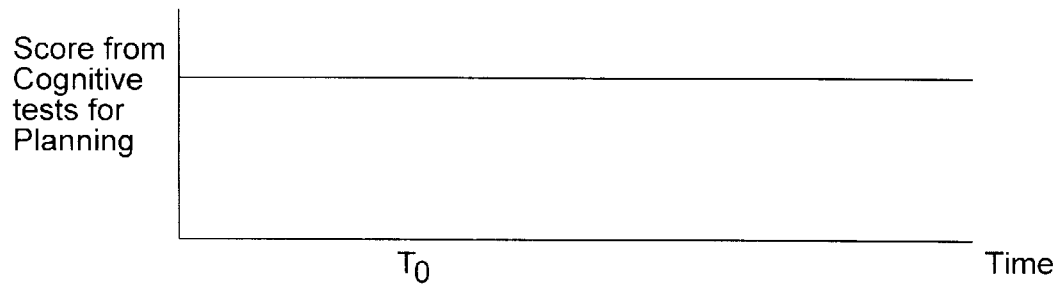
Figure 1C:
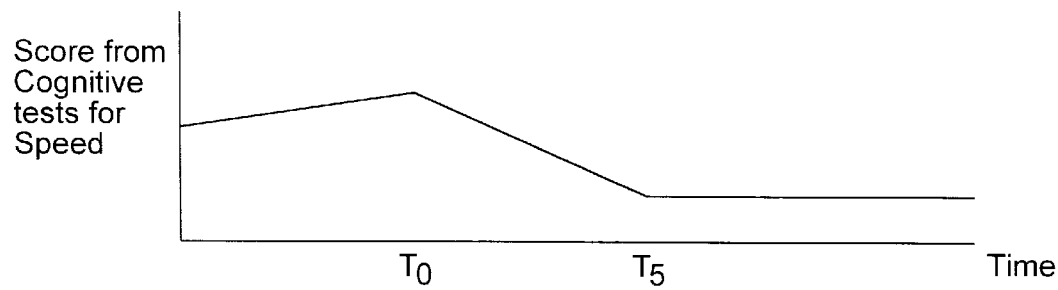

FIGS. 1a–1c illustrate examples of different responses to cognitive testing of various cognitive skills. FIGS. 1a–1c illustrate that when therapy is administered to the human subject, certain cognitive skills may be affected (as revealed by the tests) while others may not change. The cognitive test may be any cognitive test or game that probes the desired cognitive skill. For example, the maze game discussed above may be used for any of FIGS. 1a, 1b, or 1c. In addition, FIGS. 1a, 1b, and 1c illustrate different performances of a person to cognitive testing over time.

FIG. 1a illustrates, for example, the performance of a human subject to a cognitive test that tests for rule changing/switching. In this case, for example, the performance of the human subject remains constant during baseline testing and decreases linearly after administration of the biochemical based therapy is begun at inception time $T_o$.

FIG. 1b illustrates, for example, the performance of a human subject to a cognitive test that tests for planning. In this case, for example, the performance of the human subject does not change with time during baseline testing and does not change overtime with inception of biochemical based therapy.

FIG. 1c illustrates, for example, the performance of a human subject to cognitive testing that tests for speed in solving a cognitive test. In this case, for example, the performance of the human subject improves linearly over time during baseline testing, diminished after inception time $T_0$, and remains constant after time $T_5$.

In accordance with yet another aspect of the present invention, the cognitive testing techniques are optimized for fully computerized testing. That is, the test stimuli are designed to be generated by a computer or computer controlled apparatus for testing. Additionally, the responses from the test subjects are designed such that they may not require any intervention or supervision by another trained human being to administer the tests. In one embodiment of the present invention, as long as the appropriate instructions are provided to the remote testing computer, the entire testing can be performed by the test subject using a computer without involving any other person. In this manner, testing can be done with a high degree of convenience at a relatively low cost.

Figure 2:
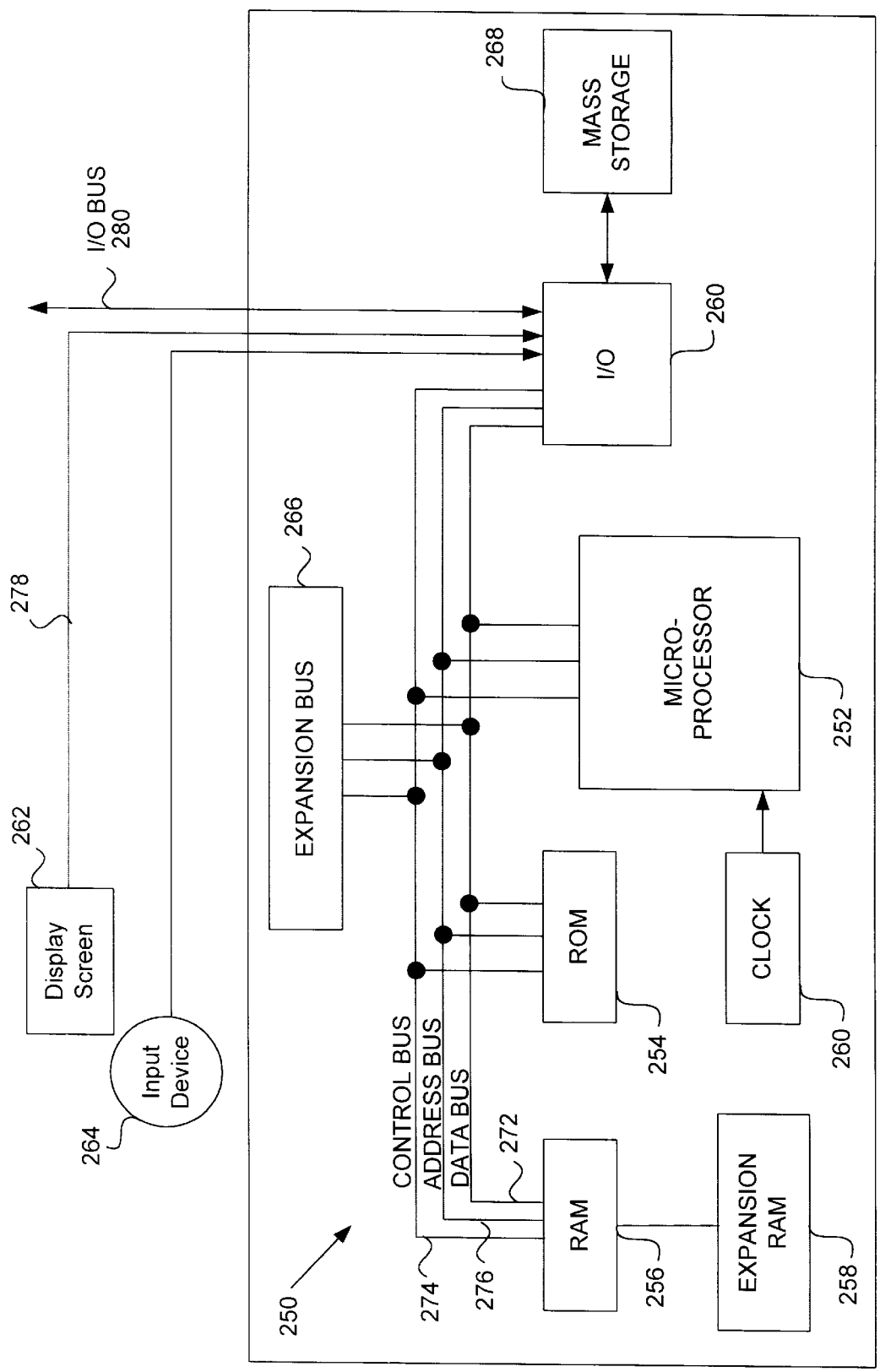
FIG. 2 shows a general purpose computer system, representing a computer suitable for implementing the present remote cognitive testing method.

In general, the cognitive tests may be generated and administered using computer-implemented techniques. FIG. 2 shows a general purpose computer system, representing a computer suitable for implementing the present inventive cognitive testing method. Referring to FIG. 2, a computer system 250 in accordance with the present invention includes a central processing unit (CPU) 252, read only memory (ROM) 254, random access memory (RAM) 256, expansion RAM 258, input/output (I/O) circuitry 260, display assembly 262, input device 264, and expansion bus 266. Computer system 250 may also optionally include a mass storage unit 268 such as a disk drive unit or nonvolatile memory such as flash memory and a real-time clock 260. In one embodiment, mass storage unit 268 may include units which utilize removable computer readable media, such as floppy disks, opto-magnetic media, optical media, and the like for the storage of programs and data.

CPU 252 is preferably a commercially available, single chip microprocessor such as one of the Intel X86 or Motorola 680XX family of chips, a reduced instruction set computer (RISC) chip such as the PowerPC™ microprocessor available from Motorola, Inc, or any other suitable processor. CPU 252 is coupled to ROM 254 by a data bus 272, control bus 274, and address bus 276. ROM 254 may partially contain the basic operating system for the computer system 250. CPU 252 is also connected to RAM 256 by busses 272, 274, and 276 to permit the use of RAM 256 as scratch pad memory. Expansion RAM 258 is optionally coupled to RAM 256 for use by CPU 252. CPU 252 is also coupled to the I/O circuitry 260 by data bus 272, control bus 274, and address bus 276 to permit data transfers with peripheral devices.

I/O circuitry 260 typically includes a number of latches, registers and direct memory access (DMA) controllers. The purpose of I/O circuitry 260 is to provide an interface between CPU 252 and such peripheral devices as display assembly 262, input device 264, mass storage 268, headphone 280, speaker 282, and/or any other I/O device. Display assembly 262 of computer system 250 is an output device for displaying objects and other visual representations of data.

The screen for display assembly 262 can be a device that uses a cathode-ray tube (CRT), liquid crystal display (LCD), or the like, of the types commercially available from a variety of manufacturers. Input device 264 can be a keyboard, a mouse, a stylus working in cooperation with a position-sensing display, or the like. Alternatively, input device 264 can be an embedded RF digitizer activated by an "active" RF stylus. As a further alternative, input device 264 may be any type of switches capable of communicating a user response to computer system 250. Therefore, as used herein, the term input device will refer to any mechanism or device for entering data and/or pointing to a particular location on a screen of a computer display. The aforementioned input devices are available from a variety of vendors and are well known in the art.

Some type of mass storage 268 is generally considered desirable. However, mass storage 268 can be eliminated by providing a sufficient amount of RAM 256 and expansion RAM 258 to store user application programs and data. In that case, RAMs 256 and 258 can optionally be provided with a backup battery to prevent the loss of data even when computer system 250 is turned off. However, it is generally desirable to have some type of long term mass storage 268 such as a commercially available hard disk drive, nonvolatile memory such as flash memory, battery backed RAM, PC-data cards, or the like.

In operation, computer system 250 is employed to generate stimuli of the various cognitive tests. These stimuli may be furnished to the test subject using any of the output devices, including display assembly 262, headphone 280, speaker 282, or any other output device. Responses from the user may then be recorded by input device 264 and analyzed by CPU 252. If desired, feedback to the user may be given at various stages of the test(s) via display assembly 262, headphone 280 or speaker 282.

It should be borne in mind that although computer system 250 is discussed in detail herein to facilitate discussion, the inventive cognitive testing technique may be practiced on a variety of suitable computer-implemented technique. By way of example, the inventive remote cognitive testing technique disclosed herein may be implemented via a computer network, such as a local area network (LAN), wide area network (WAN) or a global computer network such as the Internet. In the latter case, the inventive remote cognitive testing technique may be implemented as downloadable computer software and data (e.g., applets). The downloadable computer software and data may be kept on one or more servers on the network, accessible by any client computer or terminal capable and authorized for such access. To facilitate testing, the downloadable computer software and data can be downloaded once and reused over and over at the client computer/terminal. Alternatively, the downloadable computer software and data can be downloaded for each individual testing session via the network as needed. Network computing techniques and implementations are well known in the art and therefor are not discussed in great detail here for brevity's sake.

Figure 3:
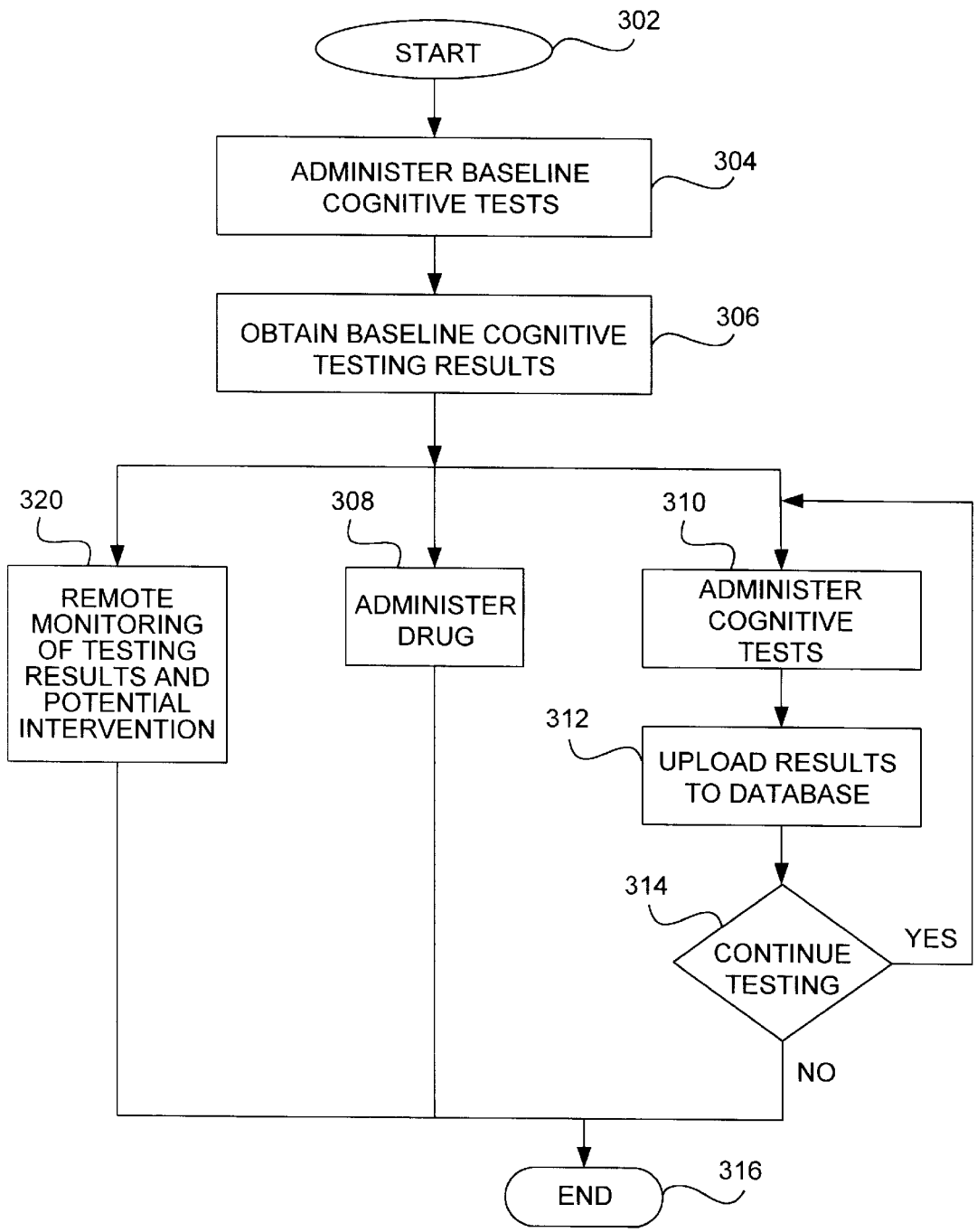
FIG. 3 illustrates, in accordance with one aspect of the present invention, the computer-implemented technique for baseline testing and remote testing of cognitive skills during a biochemical based therapy program.

FIG. 3 illustrates a method of administering cognitive testing in accordance with one embodiment of the present invention. It should be noted that prior to testing, appropriate tests for the human subject may be selected based on demographics and the proposed therapy program may also be selected. As an example, FIG. 3 shows the testing procedure for testing a specific cognitive skill once the appropriate tests are determined. It is understood that any number of other cognitive skills may be simultaneously tested and that the testing steps may vary for different cognitive skills. In step 304, a set of baseline tests is administered to obtain intrinsic cognitive skills in the human subject. These tests may be administered at an administration site or preferably using the remote computer. Preferably, the baseline testing is performed at the same time and in the same location as subsequent testing after inception of the biochemical based therapy. Thus, as mentioned before, a novel advantage of the proposed invention is the person's ability to test at home at convenient times which may improve clarity of testing assessment. This is advantageous over the prior art in which testing at an administration site may introduce random variation such as varying test times, fatigue due to travel, or mental factors involved in testing a person in an unfamiliar setting such as a hospital or an office.

In step 306, baseline intrinsic skills and data may be obtained from the person. For the case where testing is done on a remote computer at home away from the administration site, step 306 may involve transmitting data from the remote computer onto a server for the monitoring site. Steps 308, 310 and 320 may be performed concurrently. In step 308, the therapy program is administered. The therapy program may be administered for a predetermined time or the duration may be flexibly monitored. It should be borne in mind that cognitive testing may be administered for a longer or shorter period of time than the duration of the therapy program. In one embodiment of the present invention, the duration of cognitive testing may be determined by the efficacy of the therapy program in terms of degradation of a particular cognitive skill or skills.

When the therapy program begins, in accordance with one embodiment of the present invention, the cognitive testing begins at step 310 to measure the efficacy or side effects of the therapy on the particular cognitive skill or skills being tested. In step 312, the test results are transmitted to the administration site server. In step 314, a predetermined criteria can be used to determine whether testing will continue. Alternately, Step 320 is performed parallel to steps 308 and 310 and remotely monitors the results of the cognitive testing to intervene if necessary. Further, in step 320, the appropriateness of the therapy program may be monitored. For example, if significant changes in a cognitive skill are being observed, intervention of the therapy program being administered or the tests being administered may be necessary. If there is no significant decrease in performance of cognitive skills due to the therapy, then testing may be ended. Alternately, testing may also continue for purposes of data collection and building the database. Step 320 also monitors the efficacy of the therapy program for side effects. The person responsible for monitoring of the tests in step 320 may also be responsible for determining in step 314 whether testing will continue.

In accordance with one embodiment of the present invention, the high frequency testing of FIG. 3 represents remote cognitive testing on a daily basis. In another embodiment of the present invention, the high frequency testing represents remote cognitive testing twice a week. In accordance with yet another embodiment of the present invention, cognitive testing is administered multiple times per day. As can be appreciated by those skilled in the art, such frequent cognitive testing would have been prohibitively expensive if performed in accordance with prior art techniques which often require inpatient care at a medical facility.

Figure 4:
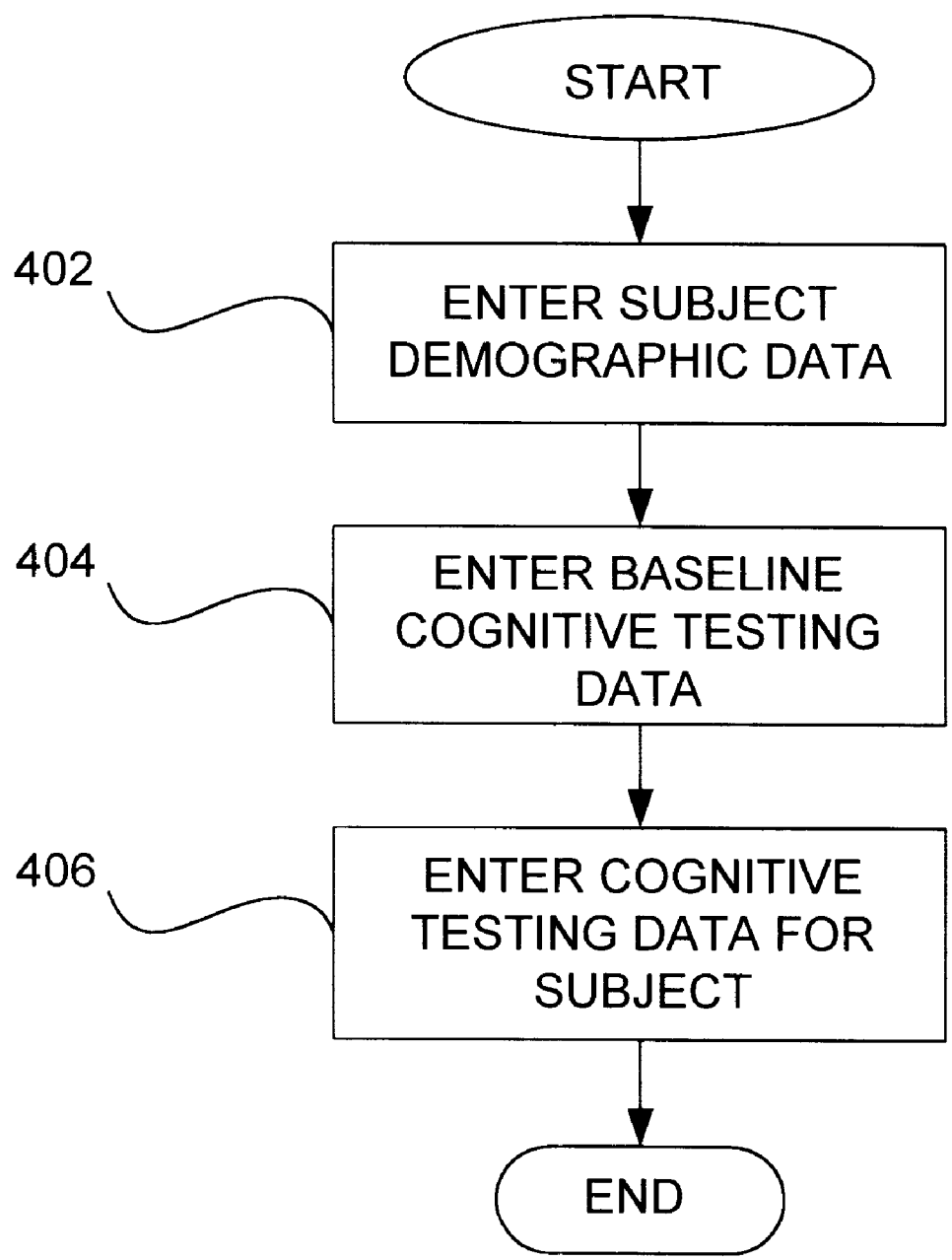
FIG. 4 illustrates, in accordance with one embodiment of the present invention, the remote computer implemented technique of building a database.

FIG. 4 illustrates, according to one embodiment of the present invention, a manner in which high frequency computer implemented cognitive testing may be used to build a database. As mentioned previously, the database may be useful in measuring the side effects a therapy program may have on a cognitive skill. In addition, the database may also be useful in selecting a therapy program based on the prior response of numerous people to previous similar therapy programs. Alternatively, the database may also be useful in assessing a person's progress with respect to previous cases. For example, if in previous specific therapy programs, a particular cognitive skill is repeatedly linearly diminished over time for hundreds of subjects, these results may be compared against the current performance of a human subject for the same therapy program to determine whether the human subject is responding as expected. In this manner, the database may flexibly be used to aid in assessment of therapy efficacy by detecting discrepancies in cognitive skill trends. In step 404, the data obtained in step 306 is entered into the database. In step 406, the remote computer implemented test results obtained in block 312 are entered for test subject. In one embodiment of the present invention, the above procedure of step 402, 404 and 406 are used to fill out one row of a database as shown in FIG. 5.

In one embodiment of the present invention, the database may be separated into demographic or other characteristics. For example, all cognitive testing responses corresponding to a specific age bracket and sex may be grouped. This may be helpful when implementing biochemical based therapy in the future by using the data to predict potential cognitive affects of a biochemical based therapy on a particular demographic group. The information from this point may further be supplied from the first monitoring computer to a second monitoring computer for additional monitoring. This may allow an individual clinician to monitor the results for numerous human subjects they are responsible for.

FIG. 5 shows one possible structure, in accordance with one embodiment of the present invention, for the database used a storing the cognitive test results of a cognitive skill in response to a therapy program for a number of people. Thus, in this case, it is common for a person to be entered in numerous databases for different cognitive skills. The number of days of baseline testing (N) and the number of days of remote cognitive testing (M) are flexibly determined and may change from person to person.

The proposed computer implemented cognitive testing is not obvious over the prior art since the prior art techniques do not address the problems solved by the proposed invention. A novel advantage of high frequency testing is improved resolution of cognitive testing data and more accessible or earlier feedback of therapy efficacy. To elaborate further, this may allow earlier intervention if necessary which may prevent long periods of exposure to negative side effects that would be felt if the testing was performed on an infrequent basis. More specifically, detecting the early warning signs of the side effects of a therapy program before they evolve into a major problem is now possible with the proposed technique. For example, in an AIDS therapy program, the high resolution of the proposed computer implemented cognitive testing method may be used to detect the early signs of dementia long before actual onset of the problem due to prolonged exposure to the therapy program.

A further advantage of the novel remote computer implemented cognitive testing method over the prior art is that a person may be tested in a familiar environment that may not introduce stresses or testing disturbances that a foreign test center may introduce. For example, in the testing of high blood pressure, it is common that the testing center itself and the travel to the testing center causes stresses that bias the high blood pressure tests. Alternatively, testing in a comfortable home setting may remove some uncontrollable testing variables which may improve cognitive testing control. Similarly, cognitive tests can be affected by unfamiliar settings or distractions. In addition, the proposed remote testing method may also allow for cognitive testing to be repetitively taken at the same time each day, allowing for improved clarity of the testing.

The high frequency testing may also allow for noise or random inputs into the testing to be filtered out, which may lead to a more accurate measure of the person's cognitive skills. For example, in the case of low frequency testing, infrequent factors such as having a bad day may largely affect the results of cognitive testing. Further, high frequency testing may allow for detection of a subtle change in cognitive skills before the person is aware.

By way of example, the proposed invention also covers computer readable medium that includes instructions for remote cognitive testing as described above. Yet another example of the present invention is a means for delivering computer readable instructions such as transmission, over a signal transmission medium, of signals representative of instructions for remote high frequency cognitive testing in a convenient manner.

While this invention has been described in terms of several preferred embodiments, there are alterations, permutations, and equivalents which fall within the scope of this invention. By way of example, cognitive tests such as numerical reasoning, pattern recognition, or testing the ability to control with a dominant hand (i.e. using a computer game) may also be utilized in the testing. It is therefore intended that the following appended claims be interpreted as including all such alterations, permutations, and equivalents as fall within the true spirit and scope of the present invention.

What is claimed is:

1. A computer implemented method for remotely administering and monitoring cognitive tests on a human subject, said method being implemented using a computer network having a monitoring computer and a remote administering computer, said remote administering computer being geographically remote from said monitoring computer and local to said human subject, said method comprising:

administering at least one baseline cognitive test to said human subject;

repeatedly performing steps a) and b) below:
 a) administering, using a remote computer implemented approach, at least one cognitive test to said human subject;
 b) obtaining, using said remote administering computer, a performance response of said human subject in said at least one cognitive test; and uploading, testing information pertaining said performance response from said administering computer via said computer network, wherein said steps a) and b) are performed a number of times effective to evaluate a cognitive level of said human subject.

2. The remote computer implemented method of claim 1 wherein said at least one baseline cognitive test includes said at least one cognitive test used after inception of a therapy program.

3. The remote computer implemented method of claim 1 wherein said at least one baseline cognitive test is administered for a duration of one week.

4. The remote computer implemented method of claim 1 wherein said at least one baseline cognitive test includes a cognitive test that tests for a cognitive skill that is substantially affected by a therapy program to be administered.

5. The remote computer implemented method of claim 1 wherein said steps a) and b) are performed on a daily basis for a number of days effective to evaluate said one of an efficacy and side effects of a therapy program.

6. The remote computer implemented method of claim 1 wherein said steps a) and b) are performed at substantially the same time each day.

7. The remote computer implemented method of claim 1 wherein said monitoring of said at least one cognitive test includes monitoring for an efficacy and side effects of a therapy program from said testing information.

8. The remote computer implemented method of claim 1 wherein said monitoring of said at least one cognitive test includes monitoring for discrepancies in cognitive skills relative to an expected performance based on prior testing of a past human subject for said cognitive tests.

9. The remote computer implemented method of claim 1 wherein said steps a) and b) are repeated for a duration that is longer than the duration of a therapy program.

10. The remote computer implemented method of claim 1 wherein said at least one baseline cognitive test includes a cognitive test that may be adapted to measure more than one cognitive skill.

11. The remote computer implemented method of claim 1 wherein said at least one cognitive test includes a cognitive test that is adaptable to measure more than one cognitive skill.

12. The remote computer implemented method of claim 1 wherein said testing information is further uploaded to another location other than the monitoring site.

13. The remote computer implemented method of claim 1 wherein different cognitive test are employed in different iterations of said performing steps a) and b).

14. The remote computer implemented method of claim 1 wherein said computer-implemented method is used to build a database.

15. The remote computer implemented method of claim 14 wherein the database includes data from baseline cognitive testing, demographic information on said human subject, said at least one cognitive test and said performance response.

16. The remote computer implemented method of claim 14 wherein the database is used in future assessment of a biochemical based therapy program.

17. A computer implemented method for remotely administering and monitoring cognitive tests on a human subject, said method being implemented using a computer network having a monitoring computer and a remote administering computer, said remote administering computer being geographically remote from said monitoring computer and local to said human subject, said method comprising:

administering at least one baseline cognitive test to said human subject, wherein said at least one baseline cognitive test includes a cognitive test that tests for a cognitive skill that is substantially affected by a therapy program to be administered;

repeatedly performing steps a) and b) below:
 a) administering, using a remote computer implemented approach, at least one cognitive test to said human subject;
 b) obtaining, using said remote administering computer, a performance response of said human subject in said at least one cognitive test; and uploading, testing information pertaining said performance response from said administering computer via said computer network, wherein said steps a) and b) are performed a number of times effective to evaluate a cognitive level of said human subject.

18. A computer implemented method for remotely administering and monitoring cognitive tests on a human subject during a therapy program, said method being implemented using a computer network having a monitoring computer and a remote administering computer, said remote administering computer being geographically remote from said monitoring computer and local to said human subject, said method comprising:

administering at least one baseline cognitive test to said human subject before inception of said therapy program;

after inception of said therapy program, repeatedly performing steps a) and b) below:

a) administering, using a remote computer implemented approach, at least one cognitive test to said human subject;

b) obtaining, using said remote administering computer, a performance response of said human subject in said at least one cognitive test;

uploading, testing information pertaining said performance response from said administering computer via said computer network, wherein said steps a) and b) are performed a number of times effective to evaluate one of an efficacy and a side effect of said therapy program; and monitoring the performance of said human subject in said at least one cognitive test.

19. A computer readable medium including instructions for remotely administering and monitoring cognitive tests on a human subject, said method being implemented using a computer network having a monitoring computer and a remote administering computer, said remote administering computer being geographically remote from said monitoring computer and local to said human subject, said instructions comprising:

instructions for administering at least one baseline cognitive test to said human subject;

instructions for repeatedly performing steps a) and b) below:

a) administering, using a remote computer implemented approach, at least one cognitive test to said human subject;

b) obtaining, using said remote administering computer, a performance response of said human subject in said at least one cognitive test; and instructions for uploading, testing information pertaining said performance response from said administering computer via said computer network, wherein said steps a) and b) are performed a number of times effective to evaluate a cognitive level of said human subject.

20. A computer implemented method for delivering computer readable instructions for remotely administering and monitoring cognitive tests on a human subject, said method being implemented using a computer network having a monitoring computer and a remote administering computer, said remote administering computer being geographically remote from said monitoring computer and local to said human subject, for a human subject, said instructions comprising:

transmitting, over a signal transmission medium, signals representative of instructions for administering a t least one baseline cognitive test to said human subject;

transmitting, over a signal transmission medium, signals representative of instructions for repeatedly performing steps a) and b) below:

a) administering, using a remote computer implemented approach, at least one cognitive test to said human subject;

b) obtaining, using said remote administering computer, a performance response of said human subject in said at least one cognitive test; and transmitting, over a signal transmission medium, signals representative of instructions for uploading, testing information pertaining said performance response from said administering computer via said computer network, wherein said steps a) and b) are performed a number of times effective to evaluate a cognitive level of said human subject.

* * * * *